United States Patent [19]

Teller et al.

[11] Patent Number: 4,600,778
[45] Date of Patent: Jul. 15, 1986

[54] PROCESS FOR THE PREPARATION OF 1,4-DIHYDROPYRIDINEDICARBOXYLIC ESTERS

[75] Inventors: Werner Teller; Wolfgang Koebernick; Arthur Haaf; Paul Naab; Michael Preiss, all of Wuppertal, Fed. Rep. of Germany

[73] Assignee: Bayer Aktiengesellschaft, Leverkusen, Fed. Rep. of Germany

[21] Appl. No.: 591,614

[22] Filed: Mar. 20, 1984

[30] Foreign Application Priority Data

Apr. 5, 1983 [DE] Fed. Rep. of Germany ....... 3312216
Apr. 5, 1983 [DE] Fed. Rep. of Germany ....... 3312283

[51] Int. Cl.$^4$ ..................... C07B 53/00; C07D 211/90
[52] U.S. Cl. ..................................... 546/249; 546/321
[58] Field of Search ................................. 546/321, 249

[56] References Cited

PUBLICATIONS

Cope, A., "Condensation Reactions I," Journal of the American Chemical Society, 59 (1937) pp. 2327–2330.
Organic Reactions, vol. 15 (1967) pp. 204–206.

Primary Examiner—Henry R. Jiles
Assistant Examiner—Dale A. Bjorkman
Attorney, Agent, or Firm—Sprung, Horn, Kramer & Woods

[57] ABSTRACT

In the preparation of a 1,4-dihydropyridine of the formula

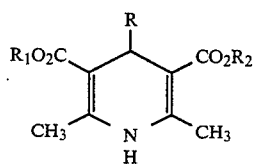

in which
R is a phenyl radical which is optionally substituted once or twice by nitro and/or chlorine,
$R_1$ is a $C_1$–$C_4$-alkyl radical which is optionally substituted by a $C_1$–$C_4$-alkoxy group, and
$R_2$ is a $C_1$–$C_{12}$-alkyl radical which is optionally substituted by a $C_1$–$C_4$-alkoxy group, a trifluoromethyl group or the radical $(C_6H_5CH_2)(CH_3)N$, by preparing an ylidene compound of the formula

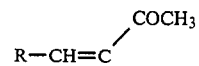

or

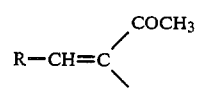

and reacting such ylidene compound with an enamine compound of the formula

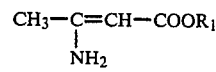

or

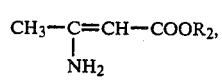

the improvement which comprises preparing the ylidene compound by reaction of a ketocarboxylic ester of the formula

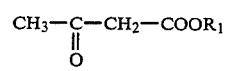

or

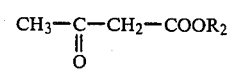

with an aldehyde of the formula RCHO, in a solvent in the presence of a catalytic amount of any acetate salt of an amine, at a temperature from about −10° C. up to 100° C. The products symmetrical or unsymmetrical, are produced in high yield and purity.

11 Claims, No Drawings

PROCESS FOR THE PREPARATION OF 1,4-DIHYDROPYRIDINEDICARBOXYLIC ESTERS

The present invention relates to a chemically original process for the preparation of known 1,4-dihydropyridinedicarboxylic esters.

Several processes for their preparation have already been disclosed.

Kirchner, Ber. 25, 2786 (1892) describes the reaction of aldehydes with 3-ketocarboxylic esters and ammonia in accordance with the reaction diagram below:

$$RCHO + 2R_1-CO-CH_2-COOR_2 + NH_3 \longrightarrow$$

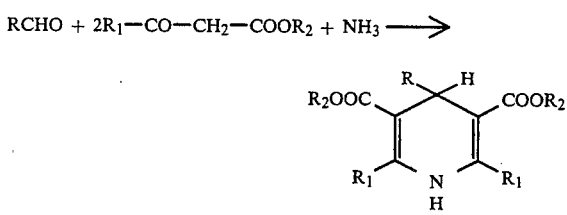

Fox et al. J. Org. Chem. 16, 1259 (1951) mentions the reaction of aldehydes with 3-ketocarboxylic esters and enaminocarboxylic esters in accordance with the reaction diagram below:

$$RCHO + R_1-CO-CH_2-COOR_2 +$$

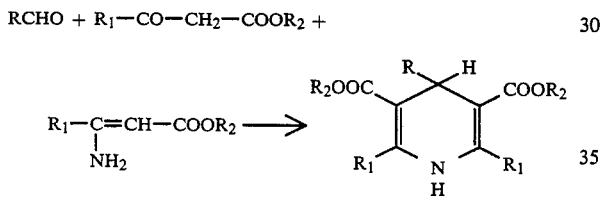

Knoevenagel, Ber. 31, 743 (1898) describes the reaction of ylidene-3-ketocarboxylic esters with enaminocarboxylic esters in accordance with the reaction diagram below:

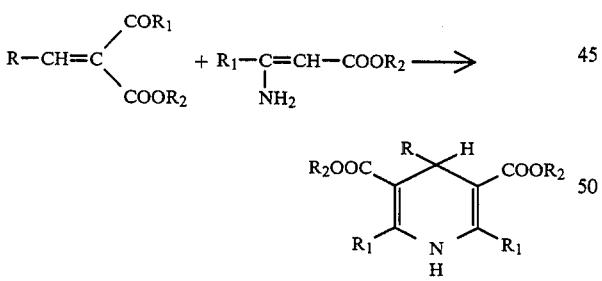

Since both aldehydes and ammonia react with ketocarboxylic esters, it may be assumed that the ylidene compound and the enamine compound are also initially formed in the two above-mentioned processes.

DE-AS (German Published Specification) No. 2,117,573 describes the one-step preparation of unsymmetrical dihydropyridines by reaction of aldehydes with ketocarboxylic acids and enaminocarboxylic esters. A two-step process is regarded as having disadvantages, since the ylidene-β-ketocarboxylic esters, which can be prepared from aldehydes and ketocarboxylic esters, are very difficult to isolate in the pure form and frequently only in low yields.

However, it emerges that one-step preparation of dihydropyridines gives rise to impurities which can be removed only with difficulty by purification processes.

Having regard to the use of the 1,4-dihydropyridines as medicaments, there is a continuous need to make these compounds available in a high degree of purity. Thus, for example, on preparation of 4-(2'-nitrophenyl)-2,6-dimethyl-3,5-dicarboethoxy-1,4-dihydropyridine by the method of U.S. Pat. No. 3,485,847, seven by-products could be detected by thin-layer chromatography.

Thus the invention relates to a process for the preparation of 1,4-dihydropyridines of the formula I

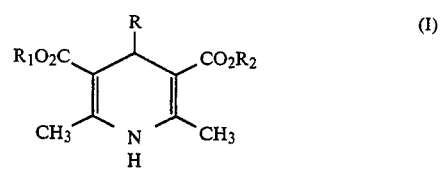

in which
R represents a phenyl radical which is optionally substituted once or twice by nitro and/or chlorine,
$R_1$ represents a $C_1$-$C_4$-alkyl radical which is optionally substituted by a $C_1$-$C_4$-alkoxy group, and
$R_2$ represents a $C_1$-$C_{12}$-alkyl radical which is optionally substituted by a $C_1$-$C_4$-alkoxy group, a trifluoromethyl group or the radical $[C_6H_5CH_2][CH_3]N-$,
by reaction of an ylidene compound of the formulae II or III

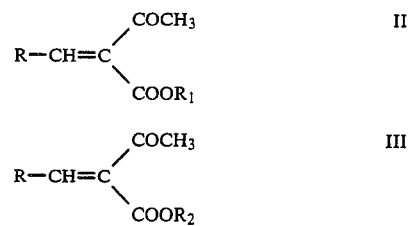

with an enamine compound of the formulae IV or V

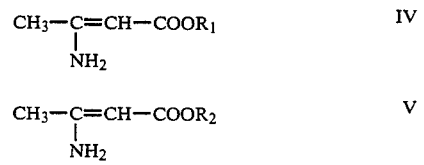

characterized in that the ylidene compounds of the formulae II or III are prepared by reaction of a ketocarboxylic ester of the formula VI or VII

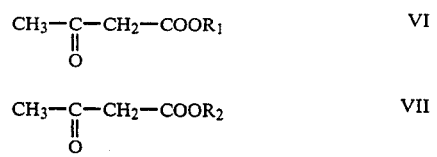

with an aldehyde of the formula RCHO, in a solvent, in the presence of catalytic amounts of acetate salts of amines, at temperatures from $-10°$ C. to $100°$ C.

Preferred acetate salts of amines which may be mentioned are: piperidine or alkylpiperidine acetate, morpholine or alkylmorpholine acetate, piperazine or alkylpiperazine acetate and pyrrolidine or alkylpyrrolidine acetate. Piperidine acetate may be mentioned in particular. The alkyl radicals in the catalysts preferably have 1-4C atoms.

The solvents which are preferably used are aliphatic alcohols, such as methanol, ethanol and/or isopropanol. The preferred reaction temperatures are 20°-60° C.

The catalyst is preferably added in amounts from 0.01 to 0.7 mole, particularly preferably from 0.02 to 0.2 mole, especially from 0.04 to 0.2 mole, per mole of ylidene compounds.

It is possible and preferred to use 1 to 2 moles, especially 1 mole, of aldehyde per mole of ketocarboxylic ester of the formula IV.

In the formula I,

R preferably denotes a 2- or 3-nitrophenyl radical, a 2- or 3-chlorophenyl radical or a 2,3-dichlorophenyl radical, $R_1$ preferably denotes methyl, ethyl, propyl, isopropyl, isobutyl or a propoxyethyl radical, and $R_2$ preferably denotes methyl, ethyl, propyl, isopropyl, isobutyl, n-decyl, methoxyethyl, propoxyethyl, trifluoromethyl, or the radical $[C_6H_5CH_2][CH_3]N$.

The reaction of the ylidene compound of the formulae II or III with the enamine compound of the formulae IV or V is carried out at temperatures from −10° to 130° C., preferably from 50° to 100° C.

It is possible and preferred to employ 1 to 1.5 moles, particularly preferably 1 to 1.3, especially 1 to 1.2 moles, of the enamine compound per mole of ylidene compound.

According to a particular embodiment, the crystalline ylidene compound remains in the reaction vessel and is directly reacted with the enamine compound.

It has to be denoted extremely surprising that, in the reaction according to the invention in the presence of the catalysts mentioned, the ylidene-3-ketocarboxylic esters are produced in high purity and excellent yield and can be very readily isolated.

Furthermore, it has to be denoted surprising that the 1,4-dihydropyridine compounds are produced in such high purity and can be isolated in the manner described. Omitting a further purification process, they contain no by-products.

The process according to the invention has a number of advantages.

Thus, the yield is higher than according to the known processes, and the isolated product need not undergo any further purification steps.

When o-nitrobenzaldehyde, methyl acetoacetate and methyl 3-aminocrotonate are used as the starting materials, then the course of the reaction can be represented by the diagram below:

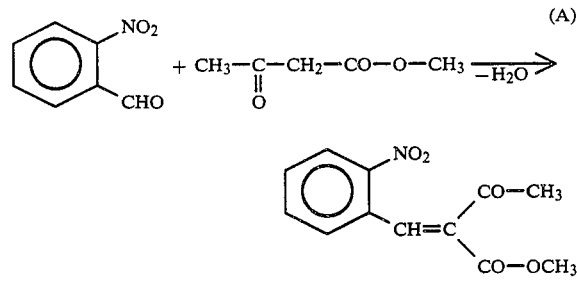

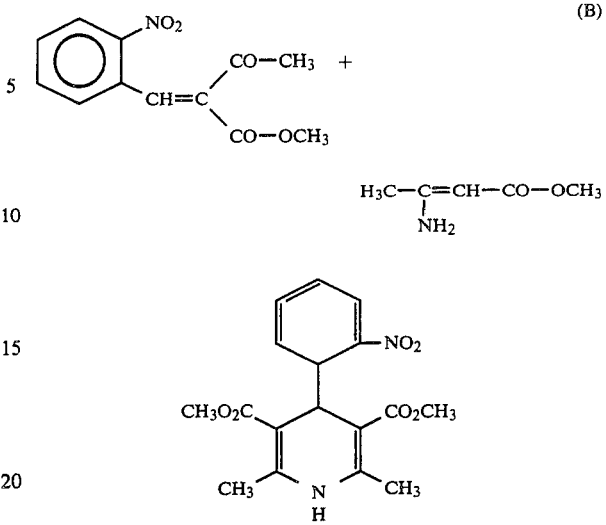

The invention may be illustrated by means of the examples which follow:

EXAMPLE 1

(a) Ylidenecarboxylic ester

In the following sequence, 80 g (0.5 mole) of 2-methoxyethyl acetoacetate, 75.5 g (0.5 mole) of 3-nitrobenzaldehyde, 1.8 g (0.03 mole) of glacial acetic acid and 2.5 g (0.03 mole) of piperidine are added, with stirring at room temperature, to 325 ml of isopropanol.

The mixture is warmed to 40° C. and kept at this temperature for 30 minutes.

It is then cooled to 20° C. and stirred for 16 hour. Thereafter it is cooled to 0° C. and stirred at this temperature for 1 hour. The supernatant solution is then removed by aspiration, and the crystals are washed with 166 ml of ice-cold isopropanol.

The resulting 2-methoxyethyl 2-(3-nitrobenzylidene)acetoacetate is immediately reacted in the same vessel, as described in (b).

If the 2-methoxyethyl 2-(3'-nitrobenzylidene)acetoacetate is isolated and dried, then 132 g of pale brown crystals are obtained (90% of the theoretical yield) of melting point 68°-72° C.

If other amounts of catalyst are employed in place of 0.03 mole of piperidine acetate, and the reaction times are varied, then the following yields are obtained:

| Amount | Yield (%) |
|---|---|
| 0.09 mole | 90.5 |
| 0.25 mole | 88.5 |

(b) 270 ml of isopropanol and 64.4 g (0.45 mole) of isopropyl 3-aminocrotonate are added to the 2-methoxyethyl 2-(3'-nitrobenzylidene)acetoacetate which has been prepared according to (a) and is moist with isopropanol. The mixture is heated to reflux (83° C.) and kept at this temperature for 24 hours.

After cooling to 0° C., the resulting crystals are isolated, washed with 86 ml of isopropanol and sucked dry.

173.2 g of 3-isopropyl, 5-(2-methoxy)-ethyl 1,4-dihydro-2,6-dimethyl-4-(3'-nitrophenyl)-3,5-pyridine dicarboxylate of melting point 122°–127° C. (92% of theory) are obtained.

Thin-layer chromatography on Merck silica gel ready-coated plates (mobile phase: chloroform:acetone:petroleum ether=3:2:5) shows no visible by-products.

EXAMPLE 2

Analogous to Example 1 ethyl 2-(3'-nitrobenzylidine)acetoacetate which has been prepared according to Example 1(a) is heated to reflux in ethanolic solution with methyl 3-aminocrotonate for ten hours. The mixture is cooled to 20° C. and kept at this temperature for 16 hours. After cooling to 5° C. the resulting crystals of 3-methyl, 5-ethyl 1,4-dihydro-2,6-dimethyl-4-(3'-nitrophenyl)-3,5-pyridine dicarboxylate of melting point 159° C. are obtained (Yield: 83% of theory).

EXAMPLE 3

(a) Ylidenecarboxylic ester

In the following sequence, 58 g (0.5 mole) of methyl acetoacetate, 82.5 g (0.5 mole) of 2,3-dichlorobenzaldehyde, 1.8 g (0.03 mole) of glacial acetic acid and 2.5 g (0.03 mole) of piperidine are added, with stirring at room temperature, to 325 ml of isopropanol.

The mixture is warmed to 40° C. and kept at this temperature for 30 minutes.

It is then cooled to 20° C. and stirred for 16 hours. Thereafter it is cooled to 0° C. and stirred at this temperature for 1 hour. The resulting methyl 2-(2,3-dichlorobenzylidene)acetoacetate is immediately reacted in the same vessel, as described in (b).

(b) 270 ml of isopropanol and 58.1 g (0.45 mole) of ethyl 3-aminocrotonate are added to the methyl 2-(2,3-dichlorobenzylidene)acetacetate which has been prepared according to (a) and is moist with isopropanol. The mixture is heated to reflux (83° C.) and kept at this temperature for 24 hours.

After cooling to 0° C., the resulting crystals are isolated, washed with 86 ml of isopropanol and sucked dry.

138 g of 3-methyl, 5-ethyl 1,4-dihydro-2,6-dimethyl-4-(2,3-dichlorophenyl)-3,5-pyridine dicarboxylate of melting point 146° C. (80% of theory) are obtained.

EXAMPLE 4

(a) Ylidenecarboxylic ester 116 g (1 mol) of methyl acetoacetate, 151 g (1 mol) of 2-nitrobenzaldehyde, 2.4 g (0.04 mol) of glacial acetic acid and 3.4 g (0.04 mol) of piperidine are added in that sequence, with stirring, to 650 ml of isopropanol at room temperature.

The mixture is warmed to 40° C. and kept at this temperature for 15 minutes.

It is then cooled to 20° C. and stirred for 16 hours. Subsequently it is cooled to 0° C. and stirred at this temperature for 1 hour. The supernatant solution is then removed by suction, and the crystals are centrifuged with 130 ml of ice-cold isopropanol and removed by suction.

The resulting methyl 2-(2'-nitrobenzylidene)acetoacetate is immediately reacted in the same vessel as described in (b).

When the methyl 2-(2'-nitrobenzylidene)acetoacetate is isolated and dried, then 241.7 g of yellow crystals (97% of the theoretical yield) of melting point 99°–101° C. are obtained.

When other amounts of catalyst are employed in place of 0.04 mol of piperidine acetate, then the following yields are obtained.

| Amount | Yield (%) |
|---|---|
| 0.08 mol | 96.5 |
| 0.16 mol | 97.6 |
| 0.5 mol | 99.9 |

(b) 750 ml of methanol and 111.5 g (0.97 mol) of methyl 3-aminocrotonate are added to the methyl 2-(2'-nitrobenzylidene)acetoacetate which has been prepared according to (a) and is moist with isopropanol. The mixture is heated to reflux (about 65° C.) and kept at this temperature for 36 hours.

After cooling to 0° C., the resulting crystals are isolated and washed with 130 ml of methanol and 500 ml of water and sucked dry.

302 g (0.87 mol) of 4-(2-nitrophenyl)-2,6-dimethyl-3,5-dicarbomethoxy-1,4-dihydropyridine of melting point 171°–175° C. (87% of the theoretical yield) are obtained.

Thin-layer chromatography on Merck silica gel ready-coated plates (mobile phase: chloroform:acetone:petroleum ether=3:2:5) shows no visible by-products.

COMPARISON EXPERIMENT

Example 1 in U.S. Pat. No. 3,485,847 was repeated and 4-(2-nitrophenyl)-2,6-dimethyl-3,5-dicarboethoxy-1,4-dihydropyridine was obtained as follows:

| Yield (%) | 80 |
|---|---|
| By-products (number) | 7 |
| Color | red-brown |

The same compound was prepared according to the above processes a and b of Example 4. The following corresponding figures were obtained:

| Yield (%) | 85 |
|---|---|
| By-products (number) | none |
| Color | yellow |

It will be appreciated that the instant specification and examples are set forth by way of illustration and not limitation, and that various modifications and changes may be made without departing from the spirit and scope of the present invention.

We claim:

1. In the preparation of a 1,4-dihydropyridine of the formula

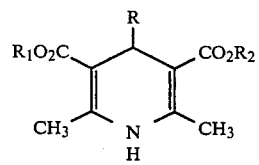

in which

R is a phenyl radical which is optionally substituted once or twice by nitro and/or chlorine, $R_1$ is a $C_1$–$C_4$-alkyl radical which is optionally substituted by a $C_1$–$C_4$-alkoxy group, and $R_2$ is a $C_1$–$C_{12}$-alkyl radical which is optionally substituted by a $C_1$–$C_4$-alkoxy group, a trifluoromethyl group or the radical $(C_6H_5CH_2)(CH_3)N$, by preparing an ylidene compound of the formula

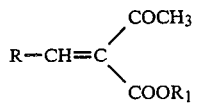

or

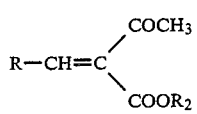

and reacting such ylidene compound with an enamine compound of the formula

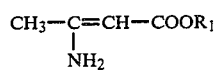

or

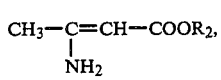

the improvement which comprises preparing the ylidene compound by reaction of a ketocarboxylic ester of the formula

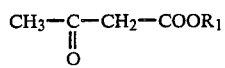

or

-continued $$CH_3-\underset{\underset{O}{\|}}{C}-CH_2-COOR_2$$

with an aldehyde of the formula RCHO, in an aliphatic alcohol as solvent in the presence of a catalytic amount of piperidine acetate, at a temperature from about $-10°$ C. up to 100° C.

2. A process according to claim 1, wherein the reaction is carried out at about 20°–60° C.

3. A process according to claim 1, wherein about 0.01 to 0.7 mole of catalyst is employed per mole of ylidene compound.

4. A process according to claim 1, wherein about 0.02 to 0.2 mole of catalyst is employed per mole of ylidene compound.

5. A process according to claim 1, wherein about 0.04 to 0.2 mole of catalyst is employed per mole of ylidene compound.

6. A process according to claim 1, wherein about 1 to 2 moles of aldehyde are employed per mole of ketocarboxylic ester.

7. A process according to claim 1, wherein about 1 mole of aldehyde is employed per mole of ketocarboxylic ester.

8. A process according to claim 1, in which
R is a 2- or 3-nitrophenyl radical, a 2- or 3-chlorophenyl radical or a 2,3-dichlorophenyl radical,
$R_1$ is a methyl, ethyl, propyl, isopropyl, isobutyl or a propoxyethyl radical, and
$R_2$ is a methyl, ethyl, propyl, isopropyl, isobutyl, n-decyl, methoxyethyl, propoxyethyl, trifluoromethylmethyl, or the radical $(C_6H_5CH_2)(CH_3)N$.

9. A process according to claim 8, wherein $R_1$ and $R_2$ are the same.

10. A process according to claim 8, wherein $R_1$ and $R_2$ are different.

11. A process according to claim 8, wherein the reaction is carried out at about 20°–60° C., about 0.04 to 0.2 mole of catalyst is employed per mole of ylidene compound, and about 1 mole of aldehyde is employed per mole of ketocarboxylic ester.

* * * * *